United States Patent
Cheney et al.

(10) Patent No.: US 6,619,954 B2
(45) Date of Patent: Sep. 16, 2003

(54) BUNDLED OPTICAL AND FLUID CONDUITS

(75) Inventors: Paul Cheney, Portland, OR (US); Eric Cheney, Portland, OR (US); Harvey Cheney, Portland, OR (US)

(73) Assignee: The Timao Group, Inc., Portland, OR (US)

( * ) Notice: Subject to any disclaimer, the term of this patent is extended or adjusted under 35 U.S.C. 154(b) by 76 days.

(21) Appl. No.: 10/007,595

(22) Filed: Nov. 9, 2001

(65) Prior Publication Data

US 2003/0091953 A1 May 15, 2003

(51) Int. Cl.$^7$ ................................................. A61C 1/00
(52) U.S. Cl. ........................................... 433/29; 433/82
(58) Field of Search .......................... 433/29, 82, 114; 600/156, 157, 158, 159

(56) References Cited

U.S. PATENT DOCUMENTS

| | | | | |
|---|---|---|---|---|
| 3,758,951 A | * | 9/1973 | Scrivo et al. | 433/29 |
| 4,629,425 A | * | 12/1986 | Detsch | 433/31 |
| 4,648,838 A | | 3/1987 | Schlachter | |
| 4,753,595 A | * | 6/1988 | Schuss et al. | 433/133 |
| 4,975,058 A | * | 12/1990 | Woodward | 433/126 |
| 5,328,365 A | * | 7/1994 | Jacoby | 433/29 |
| 5,483,951 A | * | 1/1996 | Frassica et al. | 600/104 |
| 5,913,816 A | * | 6/1999 | Sanders et al. | 600/120 |
| 6,126,592 A | * | 10/2000 | Proch et al. | 600/114 |
| 6,149,430 A | | 11/2000 | Nemetz et al. | |

* cited by examiner

Primary Examiner—Cary E. O'Connor
(74) Attorney, Agent, or Firm—Ipsolon llp

(57) ABSTRACT

An optical conduit is bundled with one or more fluid carrying conduits such that the bundled conduits are axially aligned near their distal ends. Light and fluid emitted from orifices at the terminal ends of the conduits are emitted along substantially coaxial paths. A ferrule is preferably used to bundle the conduits together at the distal ends of the conduits, and elsewhere along their combined lengths if desired. The fluid conduit may comprise an outer tube and a smaller coaxial inner tube, one tube for delivering a first fluid and the other tube for delivering a second fluid. The optical conduit comprises optical fibers for delivering light through the end of the bundle.

Because the conduits are bundled near the distal ends of the aligned tubes, the light and fluid delivered through the conduits are precisely aimed at the intended point.

20 Claims, 2 Drawing Sheets

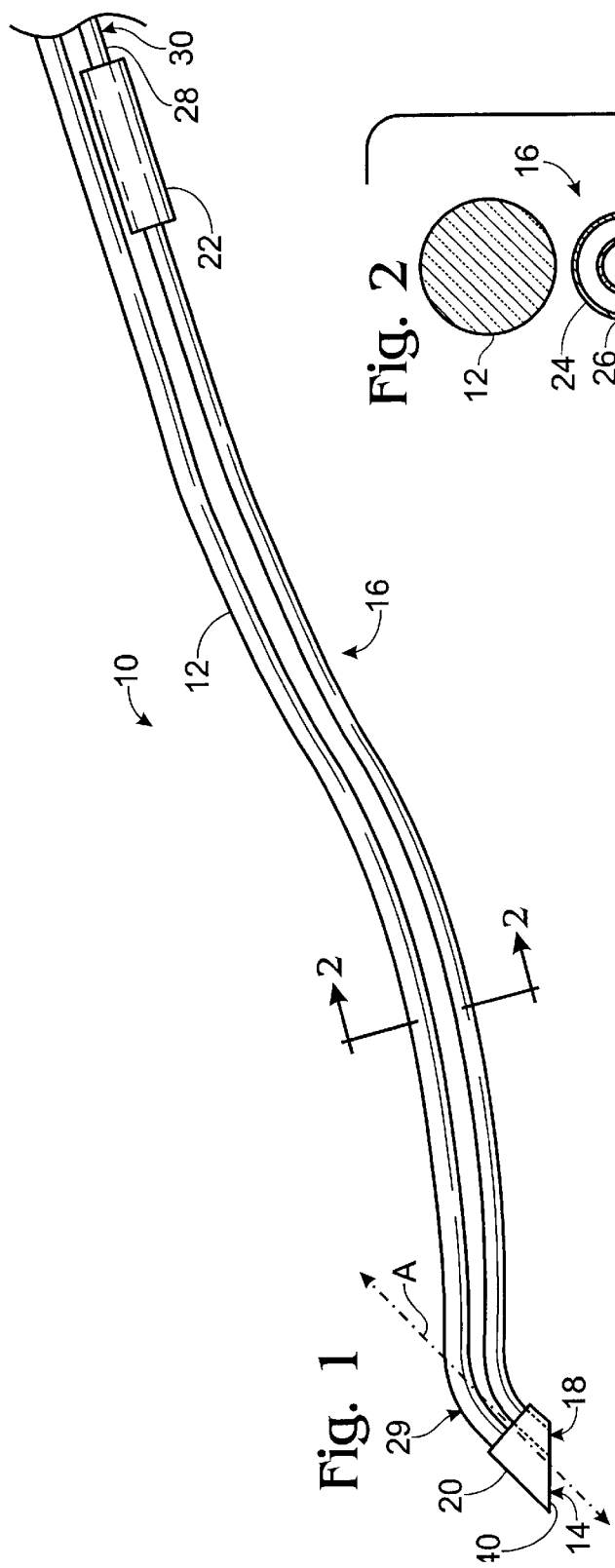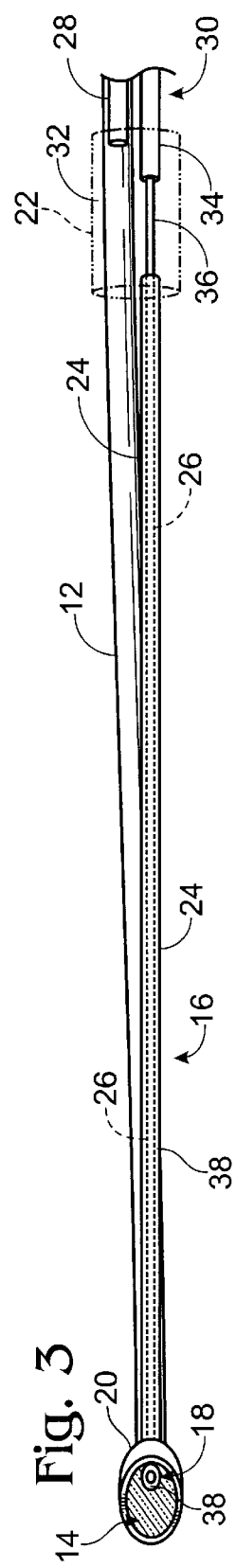

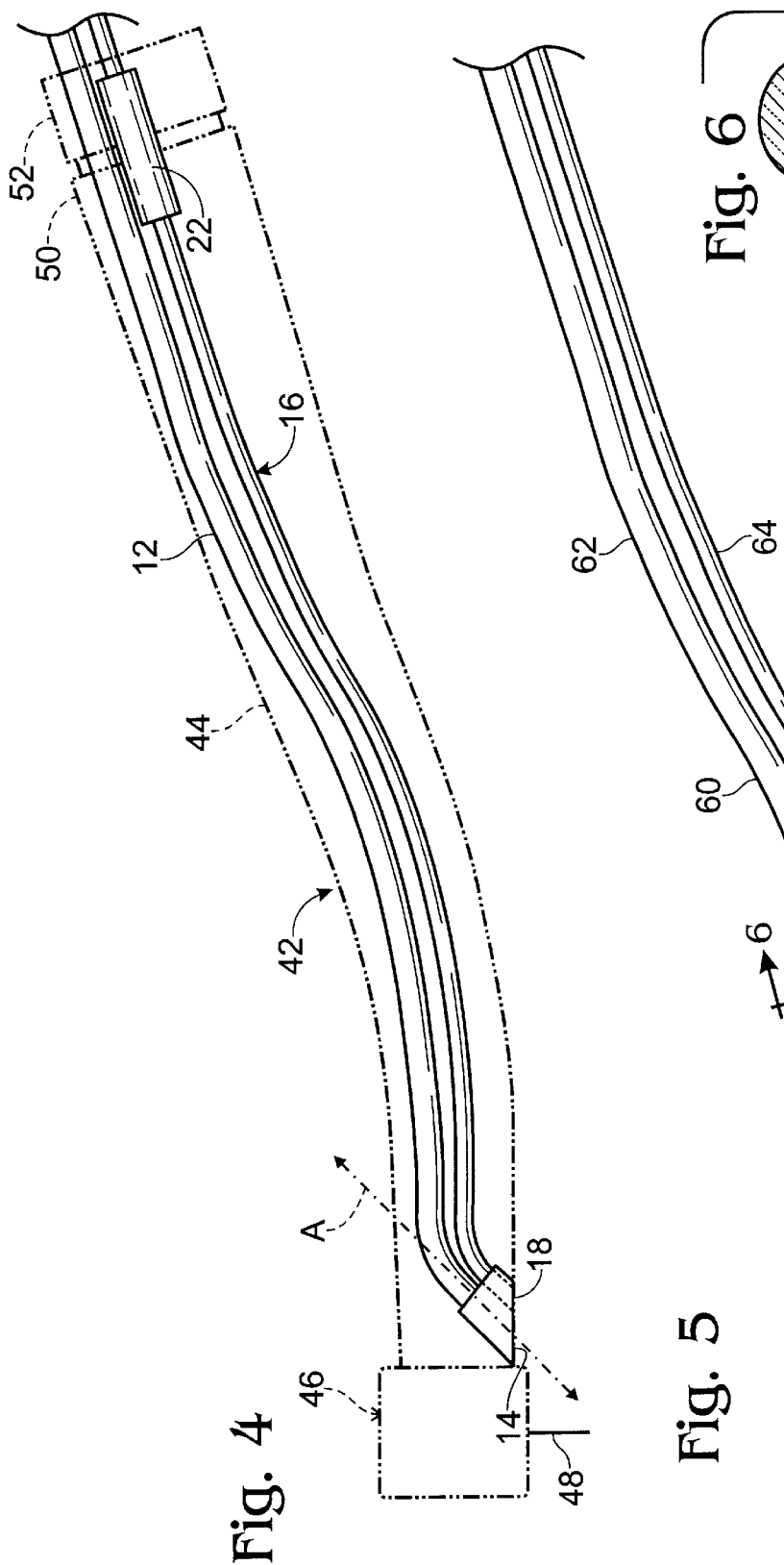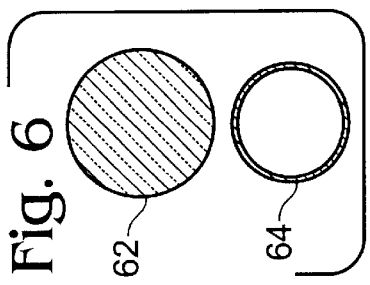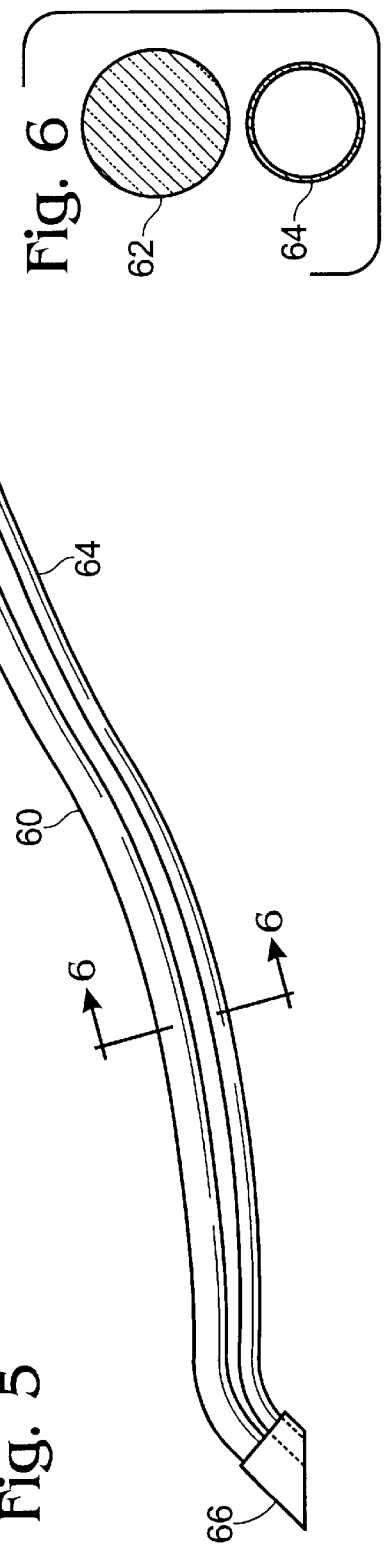

BUNDLED OPTICAL AND FLUID CONDUITS

FIELD OF THE INVENTION

This invention relates to the field of technology involving apparatus for delivering fluid and optical elements together to small areas, and more particularly to apparatus for combining optical conduits such as optical fibers and fluid conduits such as tubular members for carrying fluids into confined spaces.

BACKGROUND

When working in confined spaces, such as when a dentist is performing an intra-oral procedure on a patient, there is often a need for both optics and fluid. In such circumstances the optical component often takes the form of light being provided through an optical fiber to illuminate the work area. Likewise, the fluid component often is in the form of pressurized air or liquid, but also could be in the form of a fluid under a negative pressure such as a vacuum. The present invention relates to bundled conduits for accurately delivering optics and for carrying fluid to, or delivering fluid from the combined ends of the conduits.

The problems that the present invention addresses arise in many different fields of technology. However, they are described herein with respect to only a few of those fields, and primarily with respect to dental tools such as handpieces. Many conventional dental handpieces such as rotary tools used for drilling, cleaning and polishing include so-called chip-air and water. The air and water typically are provided to the handpiece from an external source and are fed into the proximal end of the tool through an appropriate industry standard coupling. Although there are many different configurations for routing chip air and water through the handpiece, a typical structure has, within the tool, separate fluid conduits extending from the coupling through the body of the tool, terminating at one or more orifices at the working, or distal end of the tool. The chip air and water are preferably aimed at or near the working end of the tool, for instance a burr, and are used to assist the dentist. When the dentist is drilling a tooth dust and or other particles are inevitably created. With a handpiece that provides chip air and water, the dentist may clean the working surface with either air or water, or both. Air and water may also be used to cool the working area.

Likewise, many known dental tools include equipment to deliver light through the distal end of the tool and onto the working surface of the tooth. While nearly all dentists use overhead lights to illuminate their patient's teeth, shadows caused by the dentist and tools and the like are always a problem. Light directed into the intra-oral area through the dental appliance helps alleviate the problems caused by shadow. As with chip air and water, there are many different known methods to deliver light through a handpiece. Typical among these methods include the use of fiber optic strands extending through the handpiece, and light emitting elements positioned near the distal end of the handpiece.

One example of the former technique is exemplified in U.S. Pat. No. 6,149,430, which is directed to a molded handpiece. During the molding process conduits for chip air, water and a light valve may be formed according to certain specified lost material casting processes. An example of the later is disclosed in U.S. Pat. No. 4,648,838. The handpiece described in the '838 includes a light emitting element positioned within the distal end of the canula in a position to cast light on the intra-oral region where the dentist is working. In an alternative embodiment, the light emitting element is positioned relatively more remotely from the distal end of the tool and light is transmitted to the distal end through a fiber optic bundle. As with the apparatus described in the '430 patent, the canula described in the '838 patent includes separate passageways for carrying air and water from an external source through the handpiece and to the working end of the tool.

Another known, and perhaps more typical method of delivering fluid and light through a handpiece is with standard metal (e.g. stainless steel) handpieces that have a hollow handle. In tools such as these the chip air and water may be delivered through dedicated tubing that may be suspended in the handle along a substantial length thereof between the standard coupling at the proximate end and an orifice at the distal end. Likewise, light may be provided through a fiber optic bundle that is separately routed through the handle. Like the fluid tubes, the fiber optic bundle is often suspended between the ends. In some handpieces the optical fiber bundle is bifurcated near the working end of the handpiece to provide light directed on the working tool (such as a burr) from two different angles.

Each of the handpieces disclosed in the '430 and '838 patents, and the hollow handpieces described above, represents an improvement over the art. However, each has certain disadvantages with respect to the method of delivering fluid and light to the working end of the tool.

With respect to the molded handpiece described in the '430 patent it is necessary to set the fluid-carrying conduits into the handle by including either pre-formed tubes in the mold, or as described in the patent, including in the mold fusible material that is to be removed after the handpiece has been formed. With either approach it has been found that there are several problems. Chief among these is achieving the proper "aim" for the fluid and light that is emitted out of the orifices at the working end of the tool. Thus, during the molding process the fluid tubes and the light valve (for example, fiber optic bundle) are subject to movement relative to one another and relative to the mold boundaries as the liquefied polymer is injected into the mold and during the curing process. Such movement causes relative misalignment in the direction that the orifices are aimed. Furthermore, as noted in the patent, there are limitations on the minimum diameter of a conduit formed by the lost material casting process used in the patent. When it comes to casting in the chip air and water conduits, and conduit for carrying an optical fiber, the size of the handpiece may be increased to the point where the tool is larger than dentists want to use.

With respect to the '838 patent there are the obvious limitations that are present when a light emitting element (such as an LED) are used. Although most LEDs have a relatively long life, not all light transmitted from the element will reach the area of interest. Moreover, dental tools must be sterilized before use. This is typically done in an autoclave, and the operating temperatures and pressures in an autoclave may damage an LED.

Finally, as to tubular metal handpieces, there are often problems with maintaining fluid-tight plumbing fittings that result from the high frequency vibrations caused by rotary bits that may rotate at speeds upward of 300,000 rpm. Furthermore, when a hollow handpiece is autoclaved, the internal areas of the handpiece are exposed to approximately the same temperatures as the outside. Such high temperatures over repeated cleaning cycles can severely damage the optical transmission properties of fiber optics. In contrast, with a molded handpiece such as that described in the '430 patent that has a relatively more solid handle, the internal temperature of the handle body is relatively less than the temperature of the surface during autoclaving.

A problem that is common to each of the prior art devices discussed above relates not to the structural or functional attributes of the devices, but rather to the cost. With each the handpieces noted above the manufacturing and assembly costs relating to the delivery of light and fluid to the working end of the tool is significant. As an example, with a bifurcated optical fiber light delivery system as described above, assembly of the handpiece is quite difficult since the optical fibers must be routed through the handpiece and into separate openings near the head of the unit. Routing the fibers through the handpiece is difficult enough. Placing the fibers in the correct position through the openings is much more difficult. As a result, the way that light and fluid are delivered adds a significant cost element to these units. Likewise, with a molded handpiece that routes fluid and light delivery tubes through separately molded-in apertures, it is time consuming and expensive to first correctly place in the tool the fusible material that will eventually define the apertures, then after molding, to correctly route optical fibers and the like.

There is a need, therefore, for a more efficient and efficacious structure for delivering fluid and light to the working end of a dental tool or other instrument.

SUMMARY OF THE INVENTION

The present invention addresses the need for an efficient manner of delivering fluid and optics together in a bundled package. The invention is described herein primarily with respect to its use in or with dental handpieces. However, the invention may be utilized in other tools and in other settings, a few of which are described herein. Those of ordinary skill in the art to which the invention pertains will appreciate the diverse setting in which the invention may be used.

In one embodiment the invention comprises an optical conduit that is bundled with one or more fluid conduits such that the bundled conduits are axially aligned near their distal ends so that light and fluid are emitted from orifices along substantially coaxial paths. A ferrule is preferably used to bundle the conduits together at the distal ends of the conduits, and elsewhere along their combined lengths if desired. The pre-assembled bundled unit provides significant structural and functional benefits, and significantly reduces assembly and manufacturing costs, thereby reducing unit costs.

In one embodiment the fluid conduit comprises a dual conduit that comprises an outer tube and a smaller coaxial inner tube, one tube for delivering a first fluid and the other tube for delivering a second fluid. The coaxial tubes are joined in a manifold assembly to provide a leak-free enclosure. The optical conduit may be standard bundled optical fibers for delivering light through the end of the bundle, or may be fibers suited for carrying an image over the fibers.

In one preferred embodiment the bundled conduits of the invention are incorporated into a dental handpiece such as a molded handpiece. Because the conduits are bundled near the distal ends of the aligned tubes, the light and fluid delivered through the conduits are precisely aimed at the intended targets.

BRIEF DESCRIPTION OF THE DRAWINGS

The invention will be better understood and its numerous objects and advantages will be apparent by reference to the following detailed description of the invention when taken in conjunction with the following drawings.

FIG. 1 is a side view of an optical conduit bundled with a fluid conduit according to the present invention.

FIG. 2 is a cross sectional, enlarged view of the bundled conduits illustrated in FIG. 1, taken along the line 2—2 of FIG. 1.

FIG. 3 is a bottom view of the bundled conduits shown in FIG. 1 and illustrating the manifold in phantom lines to illustrate the details of the interior of the manifold.

FIG. 4 is a side view of an optical and fluid conduit according to the present invention incorporated into a dental handpiece, which is shown in phantom lines.

FIG. 5 is a side view of an alternate embodiment of the bundled conduits of the present invention.

FIG. 6 is a cross sectional, enlarged view of the bundled conduits illustrated in FIG. 5, taken along the line 6—6 of FIG. 5.

DETAILED DESCRIPTION OF THE PREFERRED EMBODIMENTS

A preferred embodiment of bundled conduits 10 according to the present invention is shown in FIGS. 1 through 5. An alternate embodiment of the bundled conduits 10 of the present invention is shown in FIGS. 4 and 6.

With reference to FIG. 1, bundled conduits 10 comprise an optical conduit 12 that has a distal end or orifice 14, a fluid conduit 16 having a distal end or orifice 18, a ferrule 20 that bundles conduits 12 and 16 together near distal ends 14 and 18 thereof, and a manifold 22 on fluid conduit 16. Each component will be described individually.

Optical conduit 12 is preferably a bundle of non-fused oriented fiber optic strands that efficiently transmit light, either in the context of light from a source at the proximal end of conduit 12 and transmitted out of the distal end 14 to illuminate an object, or in the context of light in the form of images carried from distal end 14 to appropriate equipment at the proximal end—that is, an "image conduit." Many different commercially available types of optical fiber are useful with the present invention, and the invention is not intended to be limited to any particular type of fiber or other optical conduit. It will be appreciated that optical conduit 12 comprises hundreds of separate fiber optic strands, and therefore that distal end or orifice 18 comprises the combined distal ends of hundreds of separate fiber strands.

In the embodiment illustrated in FIGS. 1 through 4, fluid conduit 16 comprises an outer tube 24 and an inner tube 26, each of which is designed to carry a fluid from a remote source at the proximate ends of the tubes and deliver it through the distal end 18 of conduit 16. The fluids carried in the tubes typically are water in one of the tubes and air in the other, each of which is carried under pressure through the tubes. A valve system, not shown, is provided to turn the fluid flow on and off. Fluids other than air and water may be carried in the tubes. Moreover, the flow of fluid in the tubes may be from the distal end 18 toward the proximal end, as when a negative pressure or vacuum is applied to the proximal ends of the tubes or of a selected tube. And alternately, the flow of fluid in one tube may be directed from the proximate to the distal end, and the flow of fluid in the other tube may be reversed, that is, from the distal end to the proximate end.

The optical conduit 12 and fluid conduit 16 are pre-assembled with ferrule 20 in the following manner. The ferrule 20 is preferably secured in a jig or similar device.

Fluid conduit 16 is then placed into the open interior of the ferrule and is secured in position in the ferrule (as illustrated in FIG. 3) against the interior wall of the ferrule by welding or with an appropriate adhesive such as an epoxy. The distal end of the optical fiber conduit 12 is then packed into the open into the remaining open space in the interior of the ferrule, for instance, with the aid of ultrasonic vibrators. The optical fibers in optical conduit 12 are then secured in the ferrule with epoxy or other suitable adhesive. In this way the combined distal ends of the fluid conduit and optical conduits occupy the entire interior space of the ferrule. Stated another way, the hundreds of optical fibers that comprise the optical conduit 12 completely fill the space in the interior of ferrule 20 so that the fibers nearly completely surround or encapsulate the fluid conduit 16, except of course where conduit 16 is secured to the interior wall of the ferrule 20. By assembling the two conduits in this manner, coaxial delivery of light and fluid out of the conduit orifices is assured.

Referring now to FIGS. 2 and 3, outer tube 24 is configured to conduct air from an external air source to the orifice 18, and inner tube 26 is configured to conduct water from an external water source to the orifice 14. The inner tube and outer tubes define separate fluid flow paths. The two tubes 24 and 26 are joined in manifold 22, which comprises a hollow, sealed chamber. An air tube 28 and a water tube 30 enter manifold 22 at one end. The manifold is sealed to prevent leakage at the inlets where the tubes enter the manifold. In this regard the manifold and the tubes may be fabricated from any appropriate material, preferably a high quality metal that may be sealed by welding or soldering and the like. The tubes and manifold may also be other materials such as various plastics, in which case the tubes would be sealed in a different manner. In any event, air tube 28 terminates within the hollow interior 32 of manifold 22. Water tube 30 decreases in diameter within interior 32 and thus steps down in diameter from a first, larger diameter section 34 to a second, smaller diameter section 36. The step-down in the diameter of water tube 30 may be accomplished in any convenient manner so long as there is a fluid-tight connection. In the embodiment shown in FIG. 3 the smaller diameter section 36 fits into the larger diameter section 34 in a fluid-tight manner. Appropriate sealing methods may be used to ensure no leaks. In an alternate embodiment, water tube 30 could be constant diameter tubing along its entire length, or a reducing fitting may be used.

A single fluid conduit 16 exits manifold 22 and is sealed at the outlet exit point to prevent leakage of fluid from the manifold. Conduit 16, as noted above, comprises an outer tube 24 and an inner tube 26. Inner tube 26 comprises the smaller diameter section 36 of water tube 30 and extends completely through conduit 16 to distal end 18. Within interior 32 of manifold 22, there is no seal between the smaller diameter section 36 and outer tube 24. Accordingly, air injected into interior 32 of manifold 22 flows into an annular space 38 defined between the exterior of inner tube 26 and the interior of outer tube 24. (FIG. 2.) Inner tube 26 is not joined to outer tube 24. As such, the inner tube "floats" freely within the outer tube. Because there is fluid in annular space 38 between the two tubes, and because the fluid is pressurized relative to ambient pressure, the two tubes tend to remain in coaxial alignment along the entire lengths thereof, thereby maintaining the annular space.

Conduits 12 and 16 are joined near their respective distal ends 14 and 18 with ferrule 20, which preferably is a cylindrical metallic band that bundles the conduits together to prevent relative movement therebetween. The conduits 12 and 16 may be joined at other locations along their combined lengths with other ferrules. However, it is necessary only to join the conduits near their distal ends as with ferrule 20 in order to ensure that the light and fluid are emitted from orifices 14 and 18, respectively, along generally parallel paths. This ensures that the fluid and light emitted from the conduits are aimed correctly. Moreover, the combined conduits may be "bundled" in other manners that accomplish the same essential function of axial alignment of the fluid paths emitted out of the orifices. To name just one equivalent methods of bundling the conduits together, the conduits could be adhered to one another with an appropriate bonding adhesive. Those of skill in the art will readily appreciate that the particular manner in which the conduits are interconnected or bundled is not critical.

Referring again to FIG. 1 it may be seen that conduits 12 and 16 are bent downwardly at a bent region 29 near the distal ends 14 and 18. The lower edge 40 of ferrule 20 is cut at an oblique angle relative to the axis represented by arrow A, which represents the orifice axis of the conduits 12 and 16 "downstream" of bent region 29. Because conduits 12 and 16 are longitudinally coaxially aligned at ends 14 and 18, light and fluid emitted from the orifices are directed out of the orifices along coaxial paths. The orifice axis is thus the parallel axes along which light and fluid are directed out of the respective conduits through their distal ends. With reference now to FIG. 3, because lower edge 40 is cut at an oblique angle, the ferrule perimeter at lower edge 40 defines an ellipse rather than a circle. Likewise, conduits 12 and 16, both of which are cylindrical at their respective distal ends 14 and 18 define ellipses rather than circles. With respect to optical conduit 12 it has been found that the elliptical end provides an oval light pattern that gives a greater "wash" of light directed onto the working surface. Furthermore, the particular numeric aperture of the fibers at distal end 14, and the particular polishing treatment applied to the fibers is not critical to the invention.

The downward angle of the bundled conduits at bent region 29 is of course unique to the handpiece shown in FIG. 4 and there is no reason why the ends of the conduits need to be angled at any particular angle. Thus, and by way of example, the conduits could be straight and the ferrule cut at a right angle relative to the conduit orifices.

Light and fluid (both air and water) are supplied in a pressurized state to conduits 12 and 16 from an external source through appropriate couplings. In FIG. 4 the bundled conduits 10 are shown incorporated in a dental handpiece 42 comprising a body 44, a head 46 at the distal end of the body having a burr 48 extending out of the lower portion thereof, and a proximal end 50 that incorporates a standard coupling 52 that mates in a standard fashion to an external cord (not shown). Coupling 52 includes junctions for mating engagement with cooperative junctions on the external cord for power, fluid (water and air) and light for optical conduit 12.

It will be appreciated that handpiece 42 may be any type of handpiece, including molded units or units such as metal handpieces having a more substantially hollow body. Such units typically have a work piece such as burr 48 fitted to the lower end of a turbine installed of the head (not shown). It further will be appreciated that in a handpiece such as that shown in FIG. 4, there is a need for a fluid source to power the turbine. The fluid is typically pressurized air that is supplied through a separate supply tube from coupling 52 to head 46, and there typically is an exhaust tube that carries the air from the turbine out of the handpiece. The tubes for carrying the pneumatic fluid to power the turbine are not shown in the drawings.

In the case of molded handpieces, bundled conduits 10 are assembled with ferrule 20 and the combined, bundle conduits 10 are placed in the preformed mold or tool prior to injection of the liquid polymer material that comprises the integrally molded handle body. Because the conduits are bundled together with ferrule 20, the combined conduits at the bundled (distal) ends are held stationary in the tool during molding, and the conduits do not more relative to one another during the molding process. As a result, light, water and air are directed accurately out of the orifices toward the working end of the burr along substantially coaxial paths. Manifold 22 may be placed at any desired location along conduit 16, but as illustrated in FIG. 4 is preferably located near the proximal end 50 of handpiece 44. Furthermore, the manifold itself may be omitted by use of a machined orifice in the body of the handpiece that serves the same function, as for example an orifice machined into the coupling unit of a molded handpiece.

The bundled conduits 10 described above preferably include an optical conduit 12 and a fluid conduit 16 that includes coaxially aligned inner and outer tubes defining separate fluid paths for carrying separate fluids, which may be the same or different. However, the invention may be carried out with only a single fluid-carrying tube as illustrated in FIGS. 5 and 6 wherein bundled conduits 60 comprise an optical conduit 62 and a fluid conduit 64 that is a single tube. A ferrule 66 binds together the two conduits 62 and 64 as described above with respect to the embodiments of FIGS. 1 through 4.

As noted, fluid is typically directed through the fluid conduits from an external source connected to the proximate end of the fluid conduit toward the distal end (orifice) of the conduit. However, the flow direction may be reversed, as in the case where a negative pressure is applied to the proximate end of the conduit. In that case the fluid conduit provides suction at the orifice, and the suction may be used to clean, remove fluid or pick up objects. In this sense, the bundled conduits may be used in innumerable settings apart from dental tools as probes for inspecting remote or hard-to-access areas, and for retrieving objects from those areas. In such a probe the optical conduit may beneficially be utilized to transmit images from the distal end to appropriate equipment at the proximate end.

While the invention is shown and described with respect to its use with a dental handpiece such as a drill, it is not limited to use with such products. Instead, it may be used with other dental tools such as water or syringes, illuminated dental mirrors and, in the case of optical imaging with the optical fiber, as examination scopes. The invention also finds many uses in other settings, such as in a probe for retrieving objects from confined spaces.

While the present invention has been described in terms of a preferred embodiment, it will be appreciated by one of ordinary skill that the spirit and scope of the invention is not limited to those embodiments, but extend to the various modifications and equivalents as defined in the appended claims.

We claim:

1. A bundled conduit for a dental tool having a proximal end and a distal end, comprising: an optical conduit having proximal and distal ends;
   a fluid conducting conduit having proximal and distal ends, said optical and fluid conduits bundled together at said distal ends such that said conduits are in contact with one another at said distal ends.

2. The bundled conduit of claim 1 wherein said optical conduit and said fluid conducting conduit are integrally bundled together at said distal ends with a ferrule.

3. The bundled conduit of claim 2 wherein said distal ends of said optical conduit and said fluid conducting conduit define orifices for emitting light and fluid, respectively, and wherein light and fluid emitted from said conduits are emitted along substantially parallel paths.

4. The bundled conduit of claim 1 wherein said distal ends of said optical conduit and said fluid conducting conduit define orifices for emitting light and fluid, respectively, and wherein said optical conduit and said fluid conducting conduit are elongate to define longitudinal axes and are substantially cylindrical, and said orifices at said distal ends of said conduits are defined by cutting said cylinders at an oblique angle relative to the longitudinal axis.

5. The bundled conduit of claim 1 wherein said fluid conducting conduit further comprises an outer tube arid a coaxial inner tube, said outer tube and inner tube defining first and second separate fluid flow paths.

6. The bundled conduit of claim 5 in which the first flow path and the second flow path are configured for carrying separate fluids.

7. The bundled conduit of claim 6 wherein one of said fluids is a gas and the other of said conduits is a liquid.

8. The bundled conduit of claim 7 wherein both fluids are delivered to said conduits in a pressurized state from an external source.

9. The bundled conduit of claim 5 wherein said fluid conducting conduit further includes a manifold defining a fluid tight chamber, said manifold having separate first and second fluid inlets and a single fluid outlet wherein said coaxial outer tube and inner tube exit from said manifold.

10. The bundled conduit of claim 1 wherein said optical conduit further defines a plurality of oriented fiber optic strands.

11. A dental handpiece, comprising:
    an elongate body having a coupling at one end thereof configured for receiving fluid and light from external sources, and a working tool at the opposite end of said body;
    a pair of elongate conduits in said body, each of said conduits having first and second ends wherein said second ends define orifices for conducting fluid and light, respectively, out of said conduits, one of said conduits defining an optical conduit mated at the first end thereof through said coupling to said external source of light and the other of said conduits defining a fluid conducting conduit mated at the first end thereof through said coupling to said external source of fluid, said pair of elongate conduits integrally bundled together a the second ends thereof without other structures in the bundle and so that light and fluid emitted from said conduits is directed toward said working tool.

12. The dental handpiece according to claim 11 wherein the body of said handpiece is molded and wherein said optical conduit and said fluid conduit are bundled together and inserted in a casting mold prior to the molding of the handpiece.

13. The dental handpiece according to claim 12 wherein said fluid conducting conduit further defines coaxial inner and outer tubes having an annular space therebetween defining first and second fluid flow paths.

14. The dental handpiece according to claim 13 in which separate fluids are delivered said first and second flow paths.

15. The dental handpiece according to claim 13 wherein said separate fluid comprise water and air, respectively, and wherein the water and air are emitted out of said orifices along substantially parallel first and second fluid flow paths.

16. In a dental tool including a handpiece defining an elongate body, a working tool at a first end thereof and an external source of light and fluid coupled to a second end thereof the improvement comprising:

a pair of conduits contained in said elongate body, the first of said conduits defining a light-transmitting conduit coupled at a first end to said external source of light and the second of said conduits defining a fluid-transmitting conduit coupled at a first end to said external source of fluid, each of said conduits terminating at an orifice at the second ends thereof configured for directing light and fluid, respectively, along substantially coaxial flow paths toward said working tool, and wherein said conduits are connected to one another and in contact with one another adjacent the second ends.

17. The dental tool according to claim 16 in which the body is an integrally molded piece formed by injecting a liquid polymer material into a preformed mold, and wherein said pair of conduits are prebundled to one another adjacent the second ends thereof prior to insertion into said preformed mold and prior to injection of said liquid polymer material.

18. The dental tool according to claim 17 where said first and second conduits are positioned in said mold such that light and fluid emitted from said conduit orifices are directed at said working tool along substantially coaxial paths.

19. The dental tool according to claim 16 wherein said fluid transmitting conduit further defines coaxially aligned inner and outer tubular members defining first and second flow paths for transmitting first and second fluids from external sources.

20. The dental tool according to claim 19 wherein said first and second fluids are different fluids.

* * * * *